United States Patent [19]

Hajjar

[11] Patent Number: 4,609,751

[45] Date of Patent: Sep. 2, 1986

[54] METHOD OF HYDROLYZING CHLOROSILANES

[75] Inventor: Abraham L. Hajjar, Scotia, N.Y.

[73] Assignee: General Electric Company, Waterford, N.Y.

[21] Appl. No.: 524,469

[22] Filed: Aug. 18, 1983

Related U.S. Application Data

[63] Continuation-in-part of Ser. No. 330,347, Dec. 14, 1981, abandoned.

[51] Int. Cl.$^4$ ................................................. C07F 7/08
[52] U.S. Cl. ..................................... 556/456; 556/450; 556/451; 556/453; 556/459; 556/460; 528/10
[58] Field of Search ............... 556/459, 460, 453, 456, 556/450, 451; 528/10

[56] References Cited

U.S. PATENT DOCUMENTS

| | | | |
|---|---|---|---|
| 2,618,648 | 11/1952 | Bluestein | 556/460 |
| 2,641,589 | 6/1953 | Chevalier | 556/460 X |
| 2,758,124 | 8/1956 | Schwenker . | |
| 2,832,794 | 4/1958 | Gordon | 556/459 |
| 3,364,246 | 1/1968 | Rossmy . | |
| 3,627,805 | 12/1971 | Thomas et al. | 556/460 |
| 4,039,567 | 8/1977 | Kotzsch et al. . | |
| 4,221,691 | 9/1980 | Danielson et al. . | |

FOREIGN PATENT DOCUMENTS 64439  6/1975  Romania .

*Primary Examiner*—Paul F. Shaver

[57] ABSTRACT

A method is provided for hydrolyzing chlorosilanes, for example, dimethyldichlorosilane, to produce dimethylpolysiloxane hydrolyzate and an aqueous solution of hydrogen chloride along with anhydrous hydrogen chloride. Chlorosilane hydrolysis is effected in the presence of a substantially stoichiometric equivalence of water which results in the direct generation of anhydrous hydrogen chloride and a saturated aqueous hydrogen chloride solution. The saturated aqueous solution of hydrogen chloride can be recycled to the chlorosilane hydrolysis step.

6 Claims, No Drawings

METHOD OF HYDROLYZING CHLOROSILANES

This application is a continuation-in-part of Ser. No. 330,347, filed Dec. 14, 1981, now abandoned.

BACKGROUND OF THE INVENTION

The present invention relates to the hydrolysis of chlorosilanes including organochlorosilanes in a stoichiometric amount of water to produce a polysiloxane hydrolyzate and anhydrous hydrogen chloride. More particularly, the present invention relates to the hydrolysis of dimethyldichlorosilane resulting in the production of dimethylpolysiloxane hydrolyzate, anhydrous hydrogen chloride and a saturated aqueous hydrogen chloride solution which can be recycled.

Prior to the present invention, dimethyldichlorosilane was hydrolyzed in the presence of an excess amount of water to produce a dimethylpolysiloxane hydrolyzate consisting essentially of a major amount of dimethylcyclopolysiloxane and a substantially linear silanol terminated dimethylpolysiloxane. An aqueous solution of hydrogen chloride was also formed which contained a significant amount of salvageable hydrogen chloride which could be used to convert methanol to methyl chloride used in the direct method for making dimethyldichlorosilane.

One procedure for recovering the hydrogen chloride from the aqueous hydrochloric acid was to distill the mixture to produce a constant boiling HCl-H$_2$O azeotrope along with anhydrous hydrogen chloride. A significant amount of energy is required in the distillation to salvage as much of the available hydrogen chloride from the dimethyldichlorosilane hydrolysis. In An Introduction to the Chemistry of the Silicones, 2nd Edition, (1951), John Wiley & Sons, Inc., New York, E.G. Rochow indicate that, if insufficient water is supplied without a mutual solvent, part of the dimethyldichlorosilane is hydrolyzed completely to dimethylpolysiloxane and part does not react at all, or end up as linear polysiloxane with terminal halogen atoms. In addition, if hydrolysis is conducted in the presence of excess water, significant amounts of heat are generated exothermically which can result in processing problems in particular situations.

The present invention is based on the discovery that if substantially stoichiometric amounts of water are utilized to hydrolyze dimethyldichlorosilane, that anhydrous hydrogen chloride is generated directly along with a saturated solution of hydrogen chloride and water. It has been further found that additional benefits are achieved if the aqueous saturated hydrogen chloride solution is recycled to the hydrolysis reactor. In addition, it has been found that the resulting dimethylpolysiloxane is substantially the same dimethylpolysiloxane hydrolyzate produced by the procedure of the prior art utilizing excess water. Further, the method of the present invention provides anhydrous hydrogen chloride which separates from the hydrolysis mixture as it is formed during the reaction. In essence, the reactor is used as both a theoretical distillation plate and chlorosilane hydrolysis reactor.

STATEMENT OF THE INVENTION

In a chlorosilanes hydrolysis method comprising hydrolyzing chlorosilane in a stoichiometric excess of water to produce a polysiloxane hydrolyzate and an aqueous hydrogen chloride solution, whereby hydrogen chloride is recycled by heating the resulting aqueous hydrogen chloride solution obtained from the hydrolysis to form a constant boiling HCl-water azeotrope and anhydrous hydrogen chloride requiring a major amount of input energy, the improvement which comprises hydrolyzing the chlorosilane with a substantially stoichiometric equivalence of water to produce substantially the same polysiloxane hydrolyzate, anhydrous hydrogen chloride and a saturated aqueous solution of hydrogen chloride, whereby the requirement of a major amount of input energy is avoided.

In order that those skilled in the art will be better able to understand the practice of the invention reference is made to the drawing. There is shown at 10 a hydrolysis reactor which feeds into a phase separator at 20 and a storage tank at 30 which can provide for the recycling of concentrated aqueous hydrogen chloride to the aqueous feed. Multiple storage tanks, not shown, may also be used.

More particularly, water is introduced into the hydrolysis reactor at 12 and chlorosilane is introduced into the hydrolysis reactor at 11 at rates sufficient to maintain about a stoichiometric equivalence between the respective feeds. For example, a mole ratio of $$\frac{D}{H_2O} \leq \frac{1}{2}$$

can be maintained in the feed mixture, where D is dimethyldichlorosilane. The chlorosilane which can be used in the practice of the invention can be represented by the following fomula,

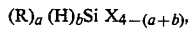

$$(R)_a(H)_b Si\, X_{4-(a+b)},$$

where R is a C$_{(1-6)}$ hydrocarbon radical selected from alkyl and aryl X is chlorine, a is an integer equal to 1 to 3 inclusive, b is a whole number equal to 0 to 2 inclusive and the sum of a +b is equal to 1 to 3. Radicals included within R are, for example, methyl, ethyl, propyl, phenyl, etc., which can be the same or different when a is greater than one.

There is immediate reaction upon contact between the chlorosilane and water. However, a temperature in the range of about 25° C. to 65° C. can be used while residence time with agitation, such as stirring, etc., can vary from about 0.1 to about 20 minutes. Higher or lower reaction times can be used if desired. Polysiloxane hydrolyzate is recovered at 21, and aqueous saturated hydrogen chloride solution is separated at 22 and fed into the storage tank at 30. In instances where the saturated aqueous hydrogen chloride solution is recycled, it is fed from 31 to the aqueous feed which is fed into the hydrolysis reactor. Anhydrous HCl may be drawn off at 14 and also at 23 and 32 for subsequent processing.

In order that those skilled in the art will be better able to practice the invention, the following examples are given by way of illustration and not by way of limitation.

EXAMPLE 1

Dimethyldichlorosilane or "D" and water were fed into a continuous hydrolysis reactor maintained at about 25° C. With a mean liquid residence time of about 5 minutes and a constant D to water molar feed ratio of 1:2, the steady state composition of the hydrolyzate gave about 51.1% octamethyltetracyclosiloxane (D$_4$)

and about 64.4% total cyclic polysiloxanes. During the same run, about 66.2% of the total chloride of the D was evolved as anhydrous HCl, with 27.6% going out as aqueous HCl which could be recovered by recycling this aqueous stream back to the hydrolysis reactor.

EXAMPLE 2

In a similar run as Example 1, but with temperature maintained at about 60° C. and a mean liquid residence time of about 15 minutes, about 87% of the total chloride of the D was evolved as anhydrous HCl with about 12.5% going out as aqueous HCl. The steady state hydrolyzate composition showed about 40% $D_4$ and 50% total cyclic polysiloxanes.

EXAMPLE 3

In this run, dimethyldichlorosilane and a 37 weight percent HCl stream were fed into a continuous hydrolysis reactor maintained at about 60° C. With a mean liquid residence time of about 12 minutes and D to water molar ratio in the inlet feed maintained at 1:4, a hydrolyzate of 52% $D_4$ and .73% total cyclics was obtained. At the same time, nearly 66% of the total chloride of the D fed was evolved as anhydrous HCl.

EXAMPLE 4

Trimethylchlorosilane or "M" and water can be fed into a continuous hydrolysis reactor maintained at about 25° C. A mean liquid residence time of about 5 minutes and an M to water molar feed ratio of about 1:1 should be utilized. The resulting product will be hexamethyldisiloxane, which is useful as a source of chainstoppers in the preparation of linear polymers.

EXAMPLE 5

Methyltrichlorosilane or "T" and wate can be fed into a continuous hydrolysis reactor maintained at about 25° C. A mean liquid residence time of about 5 minutes and a T to water molar ratio of about 1:3 should be utilized. The polymerization of the trifunctional monomer will result in the formation of three dimensional structures which are the basis of silicone resins; i.e.

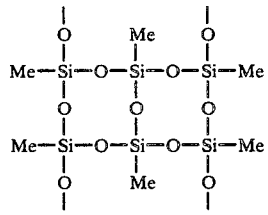

Although the above examples are directed to only a few of the very many variables in the method of the present invention, it should be understood that the present invention is directed to the hydrolysis of a much broader variety of chlorosilanes and conditions used in such hydrolysis mixtures as shown in the description preceding these examples.

What I claim as new and desire to secure by Letters Patent of the United States is:

1. In a chlorosilanes hydrolysis method comprising hydrolyzing chlorosilane in a stoichiometric excess of water to produce a polysiloxane hydrolyzate and an aqueous hydrogen chloride solution, whereby hydrogen chloride is recycled by heating the resulting aqueous hydrogen chloride solution obtained from the hydrolysis to form a constant boiling HCl-water azeotrope and anhydrous hydrogen chloride requiring a major amount of input energy, the improvement which comprises hydrolyzing the chlorosilane in substantially a stoichiometric equivalence of water to produce substantially the same polysiloxane hydrolyzate as obtained with excess water, anhydrous hydrogen chloride and a saturated aqueous solution of hydrogen chloride, whereby the requirement of a major amount of input energy is avoided.

2. A method in accordance with claim 1, where saturated aqueous hydrogen chloride is recycled to the hydrolysis reactor.

3. A method in accordance with claim 1, where anhydrous hydrogen chloride is recovered from the hydrolysis mixture.

4. In a chlorosilanes hydrolysis method comprising hydrolyzing dimethyldichlorosilane in a stoichiometric excess of water to produce a polysiloxane hydrolyzate and an aqueous hydrogen chloride solution whereby hydrogen chloride is recycled by heating the resulting aqueous hydrogen chloride solution obtained from the hydrolysis to form a constant boiling HCl-water azeotrope and anhydrous hydrogen chloride requiring a major amount of input energy, the improvement which comprises hydrolyzing the dimethyldichlorosilane in substantially a stoichiometric equivalence of water to produce substantially the same polysiloxane hydrolyzate as obtained with excess water, anhydrous hydrogen chloride and a saturated aqueous solution of hydrogen chloride, whereby the requirement of a major amount of input energy is avoided.

5. In a chlorosilanes hydrolysis method comprising hydrolyzing trimethylchlorosilane in a stoichiometric excess of water to produce a polysiloxane hydrolyzate and an aqueous hydrogen chloride solution whereby hydrogen chloride is recycled by heating the resulting aqueous hydrogen chloride solution obtained from the hydrolysis to form a constant boiling HCl-water azeotrope and anhydrous hydrogen chloride requiring a major amount of input energy, the improvement which comprises hydrolyzing the trimethylchlorosilane in substantially a stoichiometric hydrolyzate as obtained with excess water, anhydrous hydrogen chloride and a saturated aqueous solution of hydrogen chloride, whereby the requirement of a major amount of input energy is avoided.

6. In a chlorosilanes hydrolysis method comprising hydrolyzing methyltrichlorosilane in a stoichiometric excess of water to produce a polysiloxane hydrolyzate and an aqueous hydrogen chloride solution wherby hydrogen chloride is recycled by heating the resulting aqueous hydrogen chloride solution obtained from the hydrolysis to form a constant boiling HCl-water azeotrope and anhydrous hydrogen chloride requiring a major amount of input energy, the improvement which comprises hydrolyzing the methyltrichlorosilane in substantially a stoichiometric equivalence of water to produce substantially the same polysiloxane hydrolyzate as obtained with excess water, anhydrous hydrogen chloride and a saturated aqueous solution of hydrogen chloride whereby the requirement of a major amount of input energy is avoided.

* * * * *